United States Patent [19]

Manchand

[11] 4,430,507

[45] Feb. 7, 1984

[54] 4-METHYL-2-OXO-CYCLOPENTANEACETIC ACID PROSTAGLANDIN INTERMEDIATES

[75] Inventor: Percy Manchand, Montclair, N.J.

[73] Assignee: Hoffmann-La Roche Inc., Nutley, N.J.

[21] Appl. No.: 474,370

[22] Filed: Mar. 11, 1983

Related U.S. Application Data

[62] Division of Ser. No. 279,492, Jul. 1, 1981, Pat. No. 4,390,718.

[51] Int. Cl.$^3$ ............... C07C 59/46; C07C 69/732
[52] U.S. Cl. ................................. 560/122; 562/504
[58] Field of Search ..................... 560/122; 562/504

[56] References Cited

U.S. PATENT DOCUMENTS 3,897,483  7/1975  Bernady et al. ............... 562/504
4,163,109  7/1979  Teisseire et al. ............... 560/122
4,260,830  4/1981  Wilson et al. .................. 560/122

Primary Examiner—Natalie Trousof
Assistant Examiner—Patricia M. Scott
Attorney, Agent, or Firm—Jon S. Saxe; George M. Gould; William H. Epstein

[57] ABSTRACT

New optically active intermediates and processes for producing optically active prostaglandins which are useful for various therapeutic purposes such as antisecretory agents, cardiovascular agents, antiulcerogenic agents and as agents for inducing labor or terminating pregnancy in pregnant females.

4 Claims, No Drawings

4-METHYL-2-OXO-CYCLOPENTANEACETIC ACID PROSTAGLANDIN INTERMEDIATES

This is a division of application Ser. No. 279,492 filed July 1, 1981, now U.S. Pat. No. 4,390,718.

BACKGROUND OF THE INVENTION

Prostaglandins are well known therapeutic agents which have been used as cardiovscular agents, as agents to induce labor or terminate pregnancy in pregnant females, as antisecretory agents for preventing hyperacidity and as anti-ulcerogenic agents.

Prostaglandins having known therapeutic uses have been disclosed in U.S. Pat. No. 4,052,446, Holland et al., said prostaglandins having the following general formula:

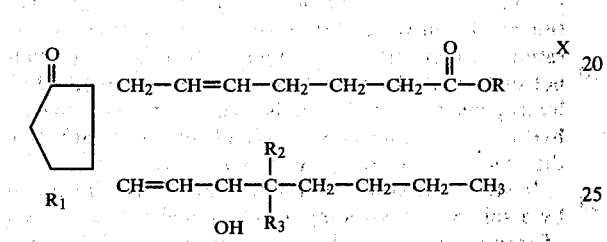

wherein R is hydrogen or lower alkyl, $R_1$ is lower alkyl, hydrogen, carboxy, lower alkoxy or carbonyl, $R_2$ is hydrogen or lower alkyl; $R_3$ is hydrogen, lower alkyl or fluoro.

Processes for the preparation and the administration of therapeutically effective prostaglandins are disclosed in the above cited U.S. patent as well as in U.S. Pat. Nos. 4,190,587 and 4,154,963.

SUMMARY OF THE INVENTION

New optically active intermediates and processes thereto are provided for use in synthesizing 2-alpha-carboxymethyl-3-beta-nitromethyl-4-alpha-methyl cyclopentan-1-one of formula

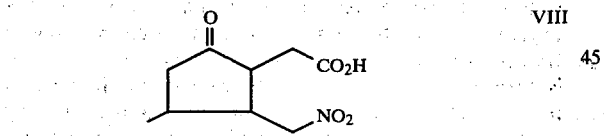  VIII which is a known intermediate for therapeutically active prostaglandins of the formula:

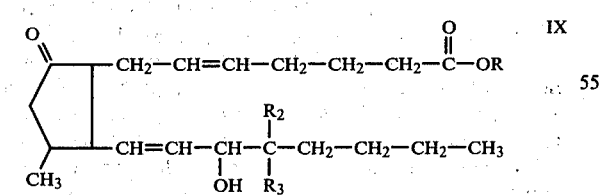  IX wherein R is hydrogen or lower alkyl, $R_2$ is hydrogen or lower alkyl and $R_3$ is hydrogen, lower alkyl or fluoro;

In accordance with this invention the compound of formula VIII, a known intermediate of prostaglandins of formula IX, is produced via the reaction of 3-methylcyclopentenone and a glyoxylate compound of formula:

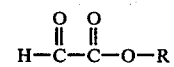  II wherein R is as above.

DETAILED DESCRIPTION OF THE INVENTION

The present invention relates to new optically active intermediates and to new processes for producing said intermediates from 3-methylcyclopentenone and a compound of formula II.

The term "lower alkyl" includes both straight chain and branched chain alkyl groups having from 1 to 7 carbon atoms such as methyl, ethyl, propyl, butyl, n-butyl, etc. The preferred alkyl groups are methyl, ethyl and n-butyl.

The following reaction scheme presents the process and intermediates in the present invention. In the scheme the reaction processes are designated as steps 1–6, while the formulas representing the starting materials, intermediates and end products are designated by Roman numerals I–VIII, and R is as defined earlier. All the compounds having an asymmetric carbon atom can be produced by the reaction processes of this scheme as racemic mixtures. It is preferred that these racemic mixtures be resolved in order to obtain optically active compounds, the preferred compounds of the present invention. These racemic mixtures may be resolved at the various steps in the process of this invention by methods well known in the art for resolving an acid or ester, providing, thereby, the optically pure enantiomers. If desired the acid of formula VIII, for example, may be resolved in accordance with the procedure disclosed in U.S. Pat. No. 4,154,963.

Reaction Scheme

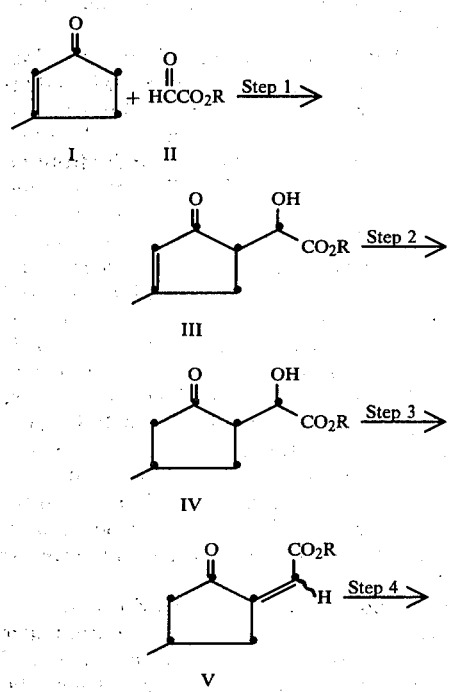

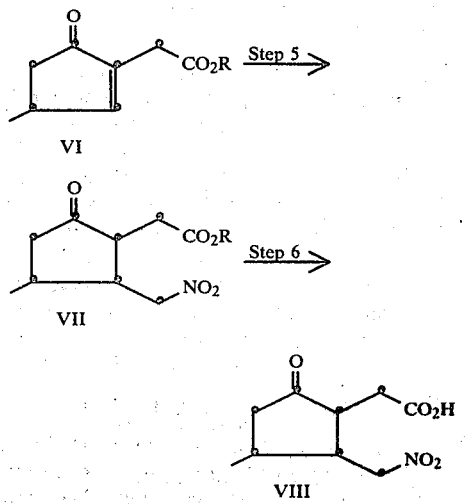

In accordance with the above reaction scheme, the process of the present invention provides the compound of formula VIII from the compounds of formulas I and II.

The starting materials for step 1 of the reaction scheme are 3-methylcyclopentenone (formula I) and a glyoxylate compound of formula II or a compound capable of liberating a glyoxylate compound of formula II. These starting materials react by an aldol condensation to form the compound of formula III. Any conventional compound liberating glyoxylate can be utilized as a starting material in this process. The preferred glyoxylates are methylglyoxylate, ethylglyoxylate and n-butyl glyoxylate or a compound liberating glyoxylate, such as polymers of the aforementioned glyoxylates. The ratio of these starting materials in the reaction mixture is not critical. It is preferred, however, that the glyoxylate be stoichiometrically in slight excess of the 3-methylcyclopentenone.

In the most preferred embodiment of this invention, 3-methylcylopentenone is reacted in step 1 with ethyl glyoxylate in a solvent containing a suitable catalyst. Any conventional inert organic solvent may be used. Among these solvents are toluene, tetrahydrofuran (THF), dimethylformamide (DMF), dimethylsulfoxide (DMSO), dimethoxyethane, (DME), etc. The preferred solvent is toluene. The amount of solvent used is not critical and can be any amount customarily recognized in the art for carrying out such a reaction. It is preferred that the solvent, such as toluene, be in an amount sufficient to dissolve all the reacting components of step 1.

A suitable catalyst may be any organic heterocyclic amine base such as morpholine, piperidine, pyrrolidine, pyridine or proline, with the preferred catalysis being morpholine. Low concentrations of catalyst are preferred such as in the range of from about 0.001% to about 10% by weight of the 3-methylcyclopentenone in the reaction mixture, with the preferred concentration being 0.05% to 5% by weight, especially preferred is 3%.

Temperature and pressure are not critical for the reaction of step 1 but it is preferably carried out under an inert gas at atmospheric pressure and temperatures of about 20° C. to reflux. It is most preferred that step 1 be carried out at the boiling point (reflux) of the reaction mixture, to provide during the reaction a monomeric glyoxylate from any polymeric form of the glyoxylate being used, resulting thereby in high yields of product. The inert gas used in carrying out this reaction and all subsequent reactions as indicated by the above scheme can be any conventional inert gas such as nitrogen or argon. The product produced in step 1 is the compound of formula III.

The condensation product, the compound of formula III, as well as the other compounds indicated in the process, may be isolated, if desired, by conventional methods well-known in the art such as distillation and chromatographic methods such as column, paper, high pressure liquid chromatography or gel filtration and the like.

Step 2 can be carried out using the isolation compound of formula III or preferably using the final reaction residue mixture of step 1 after conventional evaporation. In step 2 the double bond in the ring of the product of formula III is hydrogenated by any method of hydrogenating double bonds, such as by utilizing an hydrogenating catalyst such as palladium on charcoal in the reaction mixture carrying out this reaction.

In step 3 the compound of formula IV is dehydrated by a suitable dehydrating agent to give the compound of formula V. The dehydration process as well as the dehydrating agent may be any which are well known in the art. For example dehydration may be accomplished in a conventional manner by adding a solution of p-toluenesulfonic acid monohydrate in toluene or $P_2O_5$-alumina (neutral) in toluene. Other dehydrating agents known in the art may be conventionally used, such as $FeCl_3$, $FeCl_3$-silica gel, $BF_3$, $Et_2O$, MgO, MgO-molecular sieves, $P_2O_5$, $P_2O_5$-silica gel, anhydrous $P_2O_5$—$Al_2O_3$, $Na_2CO_3$, $Ac_2O$—HOAc, $Al_2O_3$,$CH_3SO_2CL$-pyridine, NaOAc, $CH_3SO_2Cl$—$Et_3N$ and perchloric acid. Any of the conditions conventionally used with these dehydrating agents can be used in carrying out this reaction.

In step 4 the compound of formula V is isomerized to provide the compound of formula V. The reaction of step 4 may be carried out by isomerizing in an inert organic solvent the compound of formula V using a transition metal or salt or oxide thereof as a catalyst. It is preferred that the reaction be carried out at elevated temperatures, especially at the boiling point of the solvent. In carrying out this reaction any lower alkanol may be used as the solvent. Among the preferred lower alkanols are included both straight and branched chain lower alkanols having from 1 to 7 carbon atoms, such as methyl alcohol, ethyl alcohol, butyl alcohol, propyl alcohol, etc. Ethanol is especially preferred.

This isomerization of the double bond in the compound of formula V to give the compound of formula VI may also be effected by replacing the transition metal or salt or oxide thereof with an inorganic or organic base as catalyst. For example the isomerization may be effected using pyridine as a catalystic solvent or using an alkylamine such as a dimethylaminopyridine and a solvent such as toluene or hexane as catalysts. For such a reaction the preferred temperature is from 50° C. to 130° C.

Any transition metal in pure form or salts thereof in hydrated or dehydrated form may be used in step 4 as catalysts, such as $RhCl_3.3H_2O$, $PdCl_2$, Rh,Pd, $PdCl_2(C_6H_5CN)_2$, Rh on graphite, ZnO, etc. The preferred catalyst is $RhCl_3.3H_2O$. It is preferred that the catalyst be from about 5% to about 20% by weight of the solvent. It was surprisingly found that the use of a catalyst lowered the production of unwanted isomers and the amount of reaction time. By this procedure the compound of formula VI was obtained in the absence of other significant isomers when the concentration of catalyst was 5% or more by weight of the solvent. Using less catalyst required prolonged reaction times (3-4 days) and produced compound of formula VI as a mixture with other related isomers.

The compound of formula VII can be obtained in step 5 by treating the compound of formula VI with nitromethane in the presence of a base. For carrying out the reaction of step 5 any conventional base may be used. The preferred bases are the lower alkoxides, particularly the alkali metal lower alkoxides, and the amines, particularly tertiary and quaternary amines, and pyridine. An especially preferred base is benzyltrimethylammonium hydroxide. In carrying out the reaction of step 5, temperature and pressure are not critical but the reaction is preferably carried out in an inert atmosphere such as under nitrogen and at elevated temperatures, especially preferred is 65°–70° C.

The compound of formula VIII, 2-alpha-carboxymethyl-3-beta-nitromethyl-4-alpha-methyl cyclopentan-1-one, is a known compound, disclosed for instance in U.S. Pat. No. 4,154,963 and may be obtained in step 6 by a hydrolysis of compound of formula VII. Step 5 may continue to step 6 using the isolated compound of formula VII or preferably using the final reaction residue mixture of step 5 after conventional evaporation. In carrying out the hydrolysis of the compound of formula VII any conventional method of hydrolysis may be used. Hydrolysis is preferably carried out using a dilute aqueous mineral acid such as sulfuric acid or in a dilute aqueous alkali such as sodium hydroxide. Hydrolysis in dilute sodium hydroxide is most preferred. The temperature and pressure of the hydrolysis is not critical but preferably the reaction is carried out at atmospheric pressure under nitrogen at slightly elevated temperature of about 40° C. The compound of formula VIII may then be obtained by conventional extraction and filtration methods.

The racemic products and intermediates of this invention can be resolved into their optically active components by a number of methods of resolution well know in the art. The compounds which are acids may be treated with an optically avtive base in a conventional manner to produce diasteroisomeric salts which can be separated by crystallization.

The present invention is further exemplified by the following examples.

EXAMPLE 1

Step 1 using Ethyl Glyoxylate (also known as oxoacetic acid ethyl ester):

A 2-L, round bottomed flask equipped with a mechanical stirrer and nitrogen inlet tube was charged with 48 g (0.5 M) of freshly distilled 3-methyl-2-cyclopenten-1-one (bp 73°–74° C./16 mm Hg), 66.4 g (0.65 M) of freshly distilled ethyl glyoxylate (bp 126°–130°/760 mm Hg), 1.31 g (0.015 M) of morpholine, and 650 ml of toluene. The resulting reaction mixture was boiled under reflux for 21 hours and cooled to room temperature and thereafter evaporated to provide a crude material. This crude material was used directly in the hydrogenation process of Example 3. The crude material contains the product alpha-hydroxy-(4-methyl-2-oxo-3-cyclopenten-1-yl)-acetic acid ethyl ester which may be obtained by distillation of the crude material to give the product as a viscous oil, bp 150° C./10 mm Hg.

EXAMPLE 2

Step 1 using n-Butyl Glyoxylate:

Into a 3-L, 3-necked, round-bottomed flask equipped with a mechanical stirrer, condenser, and a nitrogen inlet tube were added 96.1 g (1.0 M) of freshly distilled 3-methyl-2-cyclopenten-1-one, 169.0 g (1.3 M) of freshly distilled n-butyl glyoxylate, 1.3 L of toluene and 2.61 g (0.03 M) of morpholine. The resulting reaction mixture was heated at reflux for 24 hours and then evaporated in vacuo to give as product 263.0 g of crude racemic alpha-hydroxy-4-methyl-3-oxo-3-cyclopentene-1-acetic acid butyl ester as a viscous, light brown oil, bp 130° /0.05 mm, for use in Example 4.

EXAMPLE 3

Step 2, Hydrogenation process (Ethyl Ester):

99.1 g of crude alpha-hydroxy-(4-methyl-2-oxo-3-cyclopenten-1-yl)-acetic acid ethyl ester (as prepared in Example 1) in 882 ml of toluene was hydrogenated over 9.91 g of 10% by weight of palladium and 90% by weight of charcoal at room temperature and 25–50 psi. After hydrogen uptake had ceased, the catalyst and solvent were removed by filtration and evaporation to give 101 g of a viscous, amber-colored oil. This oil is distilled to provide the product alpha-hydroxy-4-methyl-2-oxo-cyclopentane acetic acid ethyl ester, bp 96°–111°/0.05 mmHg, for use in Example 5.

EXAMPLE 4

Step 2 Hydrogenation Process (Butyl Ester):

226 g of alpha-hydroxy-4-methyl-3-oxo-3-cyclopentene-1-acetic acid butyl ester (as prepared in Example 2) in 2 L of toluene (as solvent) was hydrogenated over 22.6 g by weight of palladium and 90% by weight of charcoal (as catalyst) at room temperature and 25–50 psi. The catalyst and solvent were removed by filtration and evaporation to provide 251 g of a reddish brown, viscous oil which was distilled to provide racemic alpha-hydroxy-4-methyl-2-oxo-cyclopentene acetic acid butyl ester, bp 110°–117° C./0.05 mmHa for use in Example 6.

EXAMPLE 5

Step 3. Dehydration (Ethyl Ester):

A 2-L, 3-necked, round-bottomed flask equipped with a mechanical stirrer, thermometer, a Dean-Stark trap and condenser was charged with 62.9 g (0.314 M) of (alpha-hydroxy-4-methyl-2-oxo-cyclopentane acetic acid ethyl ester (as prepared in Example 3) in 940 ml. of toluene and 3.0 g (0.015 M) of p-toluenesulfonic acid monohydrate. The resulting reaction mixture was stirred under nitrogen at 80° for 2 hours and then at 85° for a further 2 hours with azeotropic removal of water. The mixture was cooled to room temperature, washed successively with 250 ml of brine, 250 ml of water, dried (MgSO4), and evaporated to give 62.0 g of a dark reddish-brown oil which was distilled to provide a product as a pale homogeneous yellow oil, bp 68°–88° C./0.05 mm Hg, identified as 4-methyl-2-oxo-cyclopentylidene acetic acid ethyl ester which was used in Example 7.

EXAMPLE 6

Step 3 Dehydration (n-Butyl Ester):

Into a 5-L, 3-necked, round-bottomed flask equipped with a condenser, thermometer and nitrogen inlet were added 154.8 g (0.68 M) alpha-hydroxy-4-methyl-3-oxo-cyclopentene acetic acid butyl ester (as prepared by Example 4), 2.3 L of toluene, and 12.9 g (0.068 M) of p-toluenesulfonic acid monohydrate. The resulting reaction mixture was stirred at 75°-78° C. for 6½ hours under nitrogen. When the reaction was complete, the mixture was cooled to 15° C., poured into a separatory funnel, washed with three 1-L portions of a total of 3 L of water, dried (MgSO₄) and evaporated to give 153 g of the homogeneous 4-methyl-3-oxo-cyclopentylidene acetic acid butyl ester bp 82°-84° C./0.05 mm Hg, as a red oil for use in Example 8.

EXAMPLE 7

Step 4, Isomerization (Ethyl Ester):

A 1-L, 3-necked, round-bottomed flask equipped with a mechanical stirrer, condenser, and a nitrogen inlet tube was charged with 40.1 g of 4-methyl-2-oxo-cyclopentylidene acetic acid ethyl ester (as prepared by Example 5), 500 ml of 90% aqueous ethanol and 2.0 g of rhodium chloride trihydrate. The resulting reaction mixture (under N₂) was boiled under reflux for 14 hours, and then evaporated in vacuo. To the residue was added 200 ml of saturated brine; the mixture was then stirred for 15 minutes and extracted with three 200-mL portions, a total of 600 ml of diethyl ether. The extract was dried (MgSO₄), filtered, and the filtrate was slurried with 100 g of Grade I alumina. The alumina was filtered and washed with 400 ml of ether. The filtrate and washing were evaporated to give 31 g (77%) of product, 3-methyl-5-oxo-1-cyclopentene-1-acetic acid ethyl ester, as a colorless oil, bp 90°/0.05 mmHg, which is relatively unstable and should be refrigerated under N₂ for storage. This product was used in Example 10.

EXAMPLE 8

Step 4 Isomerization (n-Butyl Ester):

A 3-L, round-bottomed flask equipped with a mechanical stirrer, condenser, and a nitrogen inlet tube was charged with 103.8 g (0.495 M) of 4-methyl-2-oxo-cyclopentylidene acetic acid butyl ester (as prepared by Example 6), 1.25 L of 90% aq. ethanol, and 5.19 g of rhodium chloride trihydrate. The stirred mixture, under nitrogen, was heated at reflux for 24 h, cooled to 40° C., and evaporated in vacuo to give a viscous, red oil. This was diluted with 1.0 L of 20% brine and extracted with 3 × 600 ml of toluene. The combined extracts were dried with MgSO₄, concentrated to about 500 ml, and slurried with 200 g of neutral alumina (Grade I). The alumina was removed by filtration and washed three times with 250 ml of toluene. The combined filtrate and washings were evaporated to give 68.0 g (83%) of product, 3-methyl-5-oxo-1-cyclopentene-1-acetic acid ethyl ester as a pale yellow oil, bp 97°/0.05 mmHg, which is relatively unstable and should be refrigerated under nitrogen. The product was used in Example 10.

EXAMPLE 9

Alternative Isomerization Methods:

(1) A solution of 10 g of the product produced by Example 5 is placed in 100 ml of pyridine and stirred under argon at 96° C. for 23.5 hours. The solvent (pyridine) was removed in vacuo at 45° C. to give 10 g of 3-methyl-5-oxo-1-cyclopentene-1-acetic acid ethyl ester with a purity of 96% as ascertained by high-pressure liquid chromatography.

(2) A solution of 1 g of the product produced by Example 5 in 15 ml of toluene containing 100 mg 4-dimethylaminopyridine was boiled under reflux for 20 hours. The resulting mixture was cooled to room temperature and washed with 15 ml of 1 N hydrochloric acid, followed by two washes with water. The organic phase was dried over magnesium sulfate, and evaporated to give 960 mg of 3-methyl-5-oxo-1-cyclopentene-1-acetic acid ethyl ester.

EXAMPLE 10

Steps 5 and 6:

A 500-mL, round-bottomed flask was charged with 30.4 g (0.167 M) of 3-methyl-5-oxo-1-cyclopentene-1-acetic acid ethyl ester (as prepared in Example 7 or 8), 122 mL of nitromethane, and 11.7 ml of Triton B. The mixture was stirred under nitrogen at 65°-70° C. for 2 hours, cooled to 10° C., and acidified with 23 ml of cold (10° C.) 4 N H₂SO₄; stirring was continued for a further 30 minutes. The mixture was poured into 115 ml of saturated brine and extracted with 230 ml of ether. The extract was washed with saturated brine until it was neutral, dried with MgSO₄, and evaporated to give 43 g of crude product, 3-methyl-2-(nitromethyl)-5-oxo-cyclopentane acetic acid ethyl ester, as an amber colored oil.

Crude 3-methyl-2-(nitromethyl)-5-oxo-cyclopentane acetic acid ethyl ester was added to a 1-L, round-bottomed flask equipped with a mechanical stirrer, thermometer, and a nitrogen inlet tube. 355 ml of 1 N NaOH was added, and the mixture was stirred at 40° C. under nitrogen for 30 minutes. The mixture was cooled to room temperature and extracted with 150 ml of CH₂Cl₂, which was discarded. The aqueous phase was cooled to 10° C., acidified with 365 ml of cold (10° C.) 1N HCl, extracted with three 200-ml portions, a total of 600 ml of ethyl acetate, and dried (MgSO₄). To this was added 10 g of neutral decolorizing charcoal; the mixture was then slurried for a few minutes and filtered over diatomaceous earth. Evaporation of the filtrate in vacuo at less than 30° C. gave 37.4 g of 4-alpha-methyl-3-beta-nitromethyl-2-alpha-carboxymethylcyclopentanone as pale yellow crystals which was dissolved, with stirring in 90 ml of hot ethyl acetate-hexane, to produce upon filtration, 23 g (64%) of 4-alpha-methyl-3-beta-nitromethyl-2-alpha-carboxymethyl cyclopentanone as off-white crystals, mp 113°-114° C.

EXAMPLE 11

Resolution of (±)−Acid:

To a stirred heterogeneous mixture of 4.3 g (0.02 M) of 4-alpha-methyl-3-beta-nitromethyl-2-alpha-carboxymethyl cyclopentanone in 60 ml of methylene chloride was added 7.0 g (0.021 M) of strychnine under nitrogen; after about 10 minutes of stirring a homogeneous solution was obtained. The mixture was stirred, under N₂, for 2 hours, concentrated in vacuo (bath temperature) less than 30° C., preferably 25° C., and to the resulting gum (containing 5-10 ml of Ch₂Cl₂) 60 ml of acetone was added; the remaining CH₂Cl₂ was then evaporated in vacuo. The mixture was vigorously stirred at room temperature for 30 minutes and the salt of the undesired (+) acid removed by filtration; it was washed with two 30-ml portions, a total of 60 ml of acetone. The combined filtrate and washings were evaporated in vacuo (temperature less than 30° C.) to give 5.3 g of a gum, which was dissolved in 100 ml of ethyl acetate. Any insoluble material present was being removed by filtrations, washed with four 100-ml portions of a total of 400 ml of cold (15° C.) hydrochloric acid. The aqueous washes were back extracted with 100 ml of ethyl acetate and the combined extracts washed with two 100-ml portions of a total of 200 ml of water (until neutral), dried with MgSO₄, and evaporated in vacuo (−30° C.) to give an oil. This oil was dissolved in 5 ml of ethyl acetate and diluted with 5 ml of hexane. The resulting solution was left at −10° C. overnight and the crystalline racemic acid (470 mg) removed by filtration. Evaporation of the filtrate in vacuo (−30° C.) gave an oil, which was kept under high vacuum (0.1 mm/25° C.) overnight to give 1.7 g (79.5% yield) of [1R-1 alpha, 2 beta, 3 alpha)]-2-(nitromethyl)-3-methyl-5-oxo-1-cyclopentane acetic acid,. This crude material was used directly in the reduction and lactonization to give 3,3AR,4,5,6,6AS-hexahydro-4S-nitromthyl-5R-methyl-2H-cyclopenta[B] furan-]-one.

The above crude acid was crystallized from hexane to produce colorless crystals by filtration of [1R-(1 alpha, 2 beta, 3 alpha)]-2-(nitromethyl)-3-methyl-5-oxo-1-cyclopentane acetic acid, mp 56°-38° C.

What is claimed is:

1. A compound of the formula:

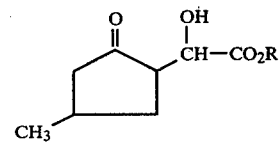

wherein R represents hydrogen or a lower alkyl.

2. The compound of claim 1 wherein R is methyl, ethyl or n-butyl.

3. The compound of claim 1 wherein said compound is alpha-hydroxy-4-methyl-2-oxocyclopentane acetic acid butyl ester.

4. The compound of claim 1 wherein said compound is alpha-hydroxy-4-methyl-2-oxocyclopentane acetic acid ethyl ester.

* * * * *